United States Patent
Takano et al.

(10) Patent No.: US 10,364,206 B2
(45) Date of Patent: Jul. 30, 2019

(54) METHOD FOR PRODUCING 2-HALOGENATED BENZOIC ACIDS

(71) Applicants: SUMITOMO SEIKA CHEMICALS CO., LTD., Kako-gun, Hyogo (JP); ZERIA PHARMACEUTICAL CO., LTD., Tokyo (JP)

(72) Inventors: Katsumi Takano, Hyogo (JP); Takeshi Fujiwara, Hyogo (JP); Hiroyuki Shiraishi, Hyogo (JP); Nami Matsuo, Hyogo (JP)

(73) Assignees: SUMITOMO SEIKA CHEMICALS CO., LTD., Kako-gun (JP); ZERIA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 15/564,902

(22) PCT Filed: Apr. 11, 2016

(86) PCT No.: PCT/JP2016/061720
§ 371 (c)(1),
(2) Date: Oct. 6, 2017

(87) PCT Pub. No.: WO2016/167225
PCT Pub. Date: Oct. 20, 2016

(65) Prior Publication Data
US 2018/0086687 A1 Mar. 29, 2018

(30) Foreign Application Priority Data
Apr. 13, 2015 (JP) .................. 2015-081727

(51) Int. Cl.
*C07C 51/363* (2006.01)
*C07C 39/00* (2006.01)
*C07C 65/21* (2006.01)
*C07B 39/00* (2006.01)
*C07C 51/42* (2006.01)

(52) U.S. Cl.
CPC ............ *C07C 51/363* (2013.01); *C07B 39/00* (2013.01); *C07C 51/42* (2013.01); *C07C 65/21* (2013.01)

(58) Field of Classification Search
CPC ........ C07C 51/363; C07C 65/21; C07B 39/00
See application file for complete search history.

(56) References Cited

U.S. PATENT DOCUMENTS

| | | | |
|---|---|---|---|
| 2,394,268 A | 2/1946 | Cecil | |
| 5,248,817 A * | 9/1993 | Auerbach | C07B 39/00 560/45 |
| 5,488,055 A | 1/1996 | Kumar et al. | |
| 2010/0111900 A1 | 5/2010 | Li et al. | |
| 2013/0253222 A1 | 9/2013 | Nakao | |
| 2014/0018415 A1 | 1/2014 | Rinsch et al. | |

FOREIGN PATENT DOCUMENTS

| | | |
|---|---|---|
| JP | 11-501924 A | 2/1999 |
| JP | 2003-252826 A | 9/2003 |
| JP | 2012-506888 A | 3/2012 |
| WO | 2012/077673 A1 | 6/2012 |
| WO | 2014/004902 A2 | 1/2014 |
| WO | 2015/146561 A1 | 10/2015 |

OTHER PUBLICATIONS

Couty, S. et al., Synthesis of 3-(arylmethylene)isoindolin-1-ones from ynamides by Heck-Suzuki-Miyaura domino reactions. Application to the synthesis of lennoxamine, 2006, Tetrahedron, 62, pp. 3882-3895 (Year: 2006).*
Stapleton, G. et al., The synthesis of some methyl-substituted Acridinecarboxylic acids, 1954, Journal of the American pharmaceutical association, vol. XLII, No. 4, consecutive No. 8 (Year: 1954).*
Auerbach, Joseph et al., "N-Bromosuccinimide/DIbromodimethylhydantoin in Aqueous Base: A Practical Method for the Bromination of Activated Benzoic Acids", Tetrahedron Letters, 1993, vol. 34, No. 6, pp. 931-934.
Alam, Ashraful et al., "Total Synthesis of 3,3', 4-tri-o-methylellagic acid from gallic acid", Tetrahedron, 2007, vol. 63, No. 42, pp. 10454-10465.
Harayama, Takashi et al., "Concise Synthesis of Fagardine and Decarine, Phenolic Benzo[c]phenanthridine Alkaloids, Using the Palladium-Assisted Biaryl Coupling Reaction", Heterocycles vol. 59, No. 1, pp. 293-301, 2003.
Nguyen, Thi-huu et al., "First General, Direct, and Regioselective Synthesis of Substituted Methoxybenzoic Acids by Ortho Metalation", Journal of Organic Chemistry, 2007, vol. 72, No. 9, pp. 3419-3429.
International Preliminary Report on Patentability (Form PCT/IB/338) issued in counterpart International Application No. PCT/JP2016/061720 dated Oct. 26, 2017, with Form PCT/IB/373 and PCT/ISA/237 (11 pages).
Extended (supplementary) European Search Report dated Nov. 2, 2018, issued in counterpart European Application No. 16780016.8. (10 pages).

* cited by examiner

*Primary Examiner* — Yate' K Cutliff
(74) *Attorney, Agent, or Firm* — Westerman, Hattori, Daniels & Adrian, LLP

(57) ABSTRACT

The purpose of the present invention is to provide a method for producing 2-halogenated benzoic acids, the method imparting high regioselectivity (high selectivity) and having a shorter reaction time than does the conventional reaction. This method for producing 2-halogenated benzoic acids, in order to achieve the above purpose, is characterized in that benzoic acids and a halogenating agent are reacted in the presence of an alkaline compound, making it possible to highly selectively obtain 2-halogenated benzoic acids.

1 Claim, No Drawings

METHOD FOR PRODUCING 2-HALOGENATED BENZOIC ACIDS

TECHNICAL FIELD

The present invention relates to a method for producing 2-halogenated benzoic acids.

BACKGROUND ART

Conventionally, a production method using a halogenating agent such as bromine in an organic solvent such as ethyl acetate (Patent Document 1) is proposed as a method for producing 2-halogenated benzoic acids. A production method using bromine to brominate benzoic acids at the 2-position in concentrated hydrochloric acid (Patent Document 2) is also proposed as a method for producing brominated benzoic acids.

PRIOR ART DOCUMENTS

Patent Documents

Patent Document 1: Japanese Laid-Open Patent Publication No. 2003-252826
Patent Document 2: WO 2012/077673

SUMMARY OF THE INVENTION

Problem to be Solved by the Invention

However, the method according to Patent Document 1 requires a long time for a reaction, and furthermore, because of low purity of acquired 2-halogenated benzoic acids, the method is not sufficiently satisfactory. Although brominated benzoic acids can be acquired at high purity in the method according to Patent Document 2 as compared to the method in Patent Document 1, a long time is required for a reaction as in the method of Patent Document 1 and, since a large amount of concentrated hydrochloric acid is used together with a reaction raw material, the method has a poor volume efficiency and is not industrially advantageous.

For example, in either of the methods of Patent Documents 1 and 2, halogenation proceeds for benzoic acids of the reaction raw material at positions other than the 2-position, resulting in generation of plural types of regioisomers. Therefore, to acquire an intended compound at high purity, the purification must be conducted to separate the intended compound from these regioisomers after the reaction. However, since these regioisomers typically have physical properties extremely close to the intended compound (2-halogenated benzoic acids), the separation is difficult and becomes a barrier to obtaining the intended compound at high purity.

The present invention was conceived in view of the situations and it is therefore an object of the present invention to provide a method for producing 2-halogenated benzoic acids capable of making a reaction time shorter and providing high regioselectivity (being highly selective).

Means for Solving Problem

The present inventors intensively studied a method for producing 2-halogenated benzoic acids. As a result, it was found that by reacting benzoic acids as a reaction raw material with a halogenating agent in the presence of an alkaline compound, the reaction promptly proceeds and 2-halogenated benzoic acids can highly selectively be acquired.

Therefore, the present invention includes the following preferred embodiments.

Item 1: A method for producing 2-halogenated benzoic acids comprising reacting benzoic acids represented by Formula (1)

[Chemical 1]

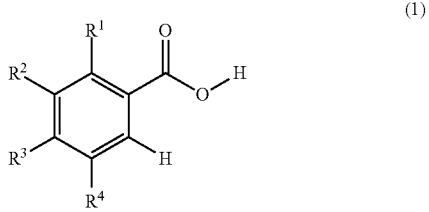

[in Formula (1), $R^1$, $R^2$, $R^3$, and $R^4$ each independently represent a hydrogen atom, an alkyl group having the carbon number of 1 to 18, an alkoxy group having the carbon number of 1 to 18, OH, COOH, $COOR^5$, or $NR^6R^7$, wherein $R^5$ represents an alkyl group having the carbon number of 1 to 18, and $R^6$ and $R^7$ each independently represent a hydrogen atom or an alkyl group having the carbon number of 1 to 18.] with a halogenating agent in the presence of an alkaline compound.

Item 2: The method for producing 2-halogenated benzoic acids according to Item 1, wherein in Formula (1), $R^1$, $R^2$, $R^3$ and $R^4$ are each independently a hydrogen atom, an alkyl group having the carbon number of 1 to 18, an alkoxy group having the carbon number of 1 to 18, COOH, or $COOR^5$, wherein $R^5$ represents an alkyl group having the carbon number of 1 to 18.

Item 3: The method for producing 2-halogenated benzoic acids according to Item 1 or 2, wherein in Formula (1), $R^1$, $R^2$, $R^3$, and $R^4$ are each independently a hydrogen atom, an alkyl group having the carbon number of 1 to 18, or an alkoxy group having the carbon number of 1 to 18.

Item 4: The method for producing 2-halogenated benzoic acids according to Item 1, 2, or 3, wherein in Formula (1), $R^1$, $R^2$, $R^3$, and $R^4$ are each independently a hydrogen atom, or an alkoxy group having the carbon number of 1 to 18.

Effect of the Invention

According to the present invention, since the reaction time can be made shorter and 2-halogenated benzoic acids can highly selectively be produced, the method is very economical and extremely industrially useful.

MODES FOR CARRYING OUT THE INVENTION

Embodiments of the present invention will now be described.

Benzoic acids serving as a reaction raw material used in the present invention are the benzoic acids represented by Formula (1).

[Chemical 2]

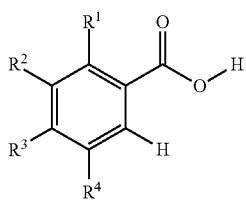

(1)

In Formula (1), $R^1$, $R^2$, $R^3$, and $R^4$ each independently represent a hydrogen atom, an alkyl group having the carbon number of 1 to 18, an alkoxy group having the carbon number of 1 to 18, OH, COOH, $COOR^5$, or $NR^6R^7$, wherein $R^5$ represents an alkyl group having the carbon number of 1 to 18, and $R^6$ and $R^7$ each independently represent a hydrogen atom or an alkyl group having the carbon number of 1 to 18.

In Formula (1), the alkyl group having the carbon number of 1 to 18 represented by $R^1$, $R^2$, $R^3$, and $R^4$ may be straight-chain, branched-chain, or cyclic and, although not particularly limited, examples include a methyl group, an ethyl group, an n-propyl group, an isopropyl group, a cyclopropyl group, an n-butyl group, an isobutyl group, a sec-butyl group, a tert-butyl group, an n-pentyl group, an isopentyl group, a sec-pentyl group, a tert-pentyl group, a neopentyl group, a 1-methylpentyl group, an n-hexyl group, an isohexyl group, a sec-hexyl group, a tert-hexyl group, a neohexyl group, a 3-methylpentyl group, an ethyl butyl group, an n-heptyl group, a 2-methylhexyl group, an n-octyl group, an isooctyl group, a tert-octyl group, a 2-ethylhexyl group, a 3-methylheptyl group, an n-nonyl group, an isononyl group, a 1-methyloctyl group, an ethylheptyl group, an n-decyl group, a 1-methylnonyl group, an n-undecyl group, a 1,1-dimethylnonyl group, an n-dodecyl group, an n-tridecyl group, an n-tetradecyl group, an n-pentadecyl group, an n-hexadecyl group, an n-heptadecyl group, an n-octadecyl group, etc. Among them, the alkyl group having the carbon number of 1 to 4 is preferably used.

In Formula (1), the alkoxy group having the carbon number of 1 to 18 represented by $R^1$, $R^2$, $R^3$, and $R^4$ may be straight-chain, branched-chain, or cyclic and, although not particularly limited, examples include a methoxy group, an ethoxy group, an n-propoxy group, an isopropoxy group, a cyclopropoxy group, an n-butoxy group, an isobutoxy group, a sec-butoxy group, a tert-butoxy group, an n-pentyloxy group, an isopentyloxy group, a sec-pentyloxy group, a tert-pentyloxy group, a neopentyloxy group, a 1-methylpentyloxy group, an n-hexyloxy group, an isohexyloxy group, a sec-hexyloxy group, a tert-hexyloxy group, a neohexyloxy group, a 2-methylpentyloxy group, a 3-methylpentyloxy group, a 1,2-dimethylbutoxy group, a 2,2-dimethylbutoxy group, a 1-ethylbutoxy group, a 2-ethylbutoxy group, an n-heptyloxy group, an isoheptyloxy group, a sec-heptyloxy group, a tert-heptyloxy group, a neoheptyloxy group, an n-octyloxy group, an isooctyloxy group, a sec-octyloxy group, a tert-octyloxy group, a neooctyloxy group, n-nonyloxy group, an isononyloxy group, a sec-nonyloxy group, a tert-nonyloxy group, a neononyloxy group, an n-decyloxy group, an isodecyloxy group, a sec-decyloxy group, a tert-decyloxy group, a neodecyloxy group, an n-undecyloxy group, an isoundecyloxy group, a sec-undecyloxy group, a tert-undecyloxy group, a neoundecyloxy group, a n-dodecyloxy group, an isododecyloxy group, a sec-dodecyloxy group, a tert-dodecyloxy group, a neodecyloxy group, an n-tridecyloxy group, an isotridecyloxy group, a sec-tridecyloxy group, a tert-tridecyloxy group, a neotridecyloxy group, an n-tetradecyloxy group, an isotetradecyloxy group, a sec-tetradecyloxy group, a tert-tetradecyloxy group, a neotetradecyloxy group, an n-pentadecyloxy group, an isopentadecyloxy group, a sec-pentadecyloxy group, a tert-pentadecyloxy group, a neopentadecyloxy group, an n-hexadecyloxy group, a sec-hexadecyloxy group, a tert-hexadecyloxy group, a neohexadecyloxy group, an n-heptadecyloxy group, an isoheptadecyloxy group, a sec-heptadecyloxy group, a tert-heptadecyloxy group, a neoheptadecyloxy group, an n-octadecyloxy group, an isooctadecyloxy group, a sec-octadecyloxy group, a tert-octadecyloxy group, a neooctadecyloxy group, etc. Among them, the methoxy group, the ethoxy group, the n-propoxy group, the isopropoxy group, the cyclopropoxy group, the n-butoxy group, the isobutoxy group, the sec-butoxy group, and the tert-butoxy group are preferably used, and the methoxy group and the ethoxy group are more preferable.

In $COOR^5$ represented by $R^1$, $R^2$, $R^3$, and $R^4$ in Formula (1), $R^5$ represents an alkyl group having the carbon number of 1 to 18. The alkyl group having the carbon number of 1 to 18 represented by $R^5$ may be straight-chain, branched-chain, or cyclic. Although not particularly limited, examples of the alkyl group having the carbon number of 1 to 18 include those exemplified as $R^1$, $R^2$, $R^3$, and $R^4$ described above.

In $NR^6R^7$ represented by $R^1$, $R^2$, $R^3$, and $R^4$ in Formula (1), $R^6$ and $R^7$ each independently represent a hydrogen atom or an alkyl group having the carbon number of 1 to 18. The alkyl group having the carbon number of 1 to 18 represented by $R^6$ and $R^7$ may be straight-chain, branched-chain, or cyclic. Although not particularly limited, examples of the alkyl group having the carbon number of 1 to 18 include those exemplified as $R^1$, $R^2$, $R^3$, and $R^4$ described above.

In Formula (1), when at least two of $R^1$, $R^2$, $R^3$, and $R^4$ are groups capable of bonding to each other to form a ring, the groups may bond to each other to form a saturated or unsaturated ring without substitution or with a substituent.

In a preferable embodiment, in Formula (1), $R^1$, $R^2$, $R^3$, and $R^4$ are each independently a hydrogen atom, an alkyl group having the carbon number of 1 to 18, an alkoxy group having the carbon number of 1 to 18, COOH, or $COOR^5$ (where $R^5$ represents an alkyl group having the carbon number of 1 to 18) among them from the viewpoint of availability etc.

In a preferable embodiment, in Formula (1), $R^1$, $R^2$, $R^3$, and $R^4$ are each independently a hydrogen atom, an alkyl group having the carbon number of 1 to 18, or an alkoxy group having the carbon number of 1 to 18 among them because an electron-donating group increases the reactivity of benzoic acids.

In a preferable embodiment, in Formula (1), $R^1$, $R^2$, $R^3$, and $R^4$ are each independently a hydrogen atom, or an alkoxy group having the carbon number of 1 to 18.

In another preferable embodiment, in Formula (1), at least one of $R^1$, $R^2$, $R^3$, and $R^4$ is an alkyl group having the carbon number of 1 to 18, or an alkoxy group having the carbon number of 1 to 18.

In a preferable embodiment, in Formula (1), one or two of $R^1$, $R^2$, $R^3$, and $R^4$ are each independently an alkyl group having the carbon number of 1 to 18, or an alkoxy group having the carbon number of 1 to 18, and those other than the alkyl group having the carbon number of 1 to 18 or the alkoxy group having the carbon number of 1 to 18 are hydrogen atoms.

In a preferable embodiment, in Formula (1), $R^1$ and $R^4$ are hydrogen atoms, and one or two of $R^2$ and $R^3$ are an alkyl group having the carbon number of 1 to 18 and/or an alkoxy group having the carbon number of 1 to 18, while any of $R^2$ and $R^3$ other than the alkyl group having the carbon number of 1 to 18 or the alkoxy group having the carbon number of 1 to 18 is a hydrogen atom.

In a preferable embodiment, the benzoic acids represented by Formula (1) are 3,4-dialkoxybenzoic acid.

In a preferred embodiment, the benzoic acids represented by formula (1) are 3,4-dimethoxybenzoic acid.

In the method for producing 2-halogenated benzoic acids of the present invention, the halogenating agent to be used is selected from the group consisting of iodinating agents, brominating agents, chlorinating agents, and mixtures thereof, for example. Specific examples include halogen molecules such as iodine, chlorine, and bromine, mixing halogen molecules such as bromine chloride (BrCl) and iodine bromide (IBr), haloimides such as N-chlorosuccinimide, N-bromosuccinimide (NBS), and DBH (1,3-dibromo-5,5-dimethylhydantoin) and hypohalites such as sodium hypoiodite, sodium hypochlorite, and sodium hypobromite (NaBrO). The halogenating agent applicable to the present invention are not limited to the halogenating agents described above, and halogenating agents generally used in organic synthesis are usable. These halogenating agents may be used singly, or two or more of the halogenating agents may be used in combination. When two or more halogenating agents are used, halogenating agents having the same halogen species are preferably selected.

Among them, preferably, the halogenating agent is iodine, sodium hypoiodite, sodium hypobromite (NaBrO), N-bromosuccinimide (NBS), DBH (1,3-dibromo-5,5-dimethylhydantoin), or bromine.

Although an amount of the halogenating agent to be used may be an amount allowing the reaction to sufficiently proceed and is not particularly limited, the amount is preferably 0.5 to 10 equivalents, more preferably 1.0 to 2.0 equivalents, relative to one equivalent of the benzoic acids represented by Formula (1), from the viewpoint of economic efficiency etc. It is considered that the halogenating agent used in the method for producing 2-halogenated benzoic acids of the present invention is partially turned into and reacted as a hypohalous acid (HXO; where X represents a halogen atom).

The alkaline compound used in the present invention may be either an inorganic alkaline compound or an organic alkaline compound.

Preferably, the inorganic alkaline compound is used. Using the inorganic alkaline compound can make production more industrially advantageous because the compound is readily available and can easily be handled.

Examples of the inorganic alkaline compound include sodium hydroxide, potassium hydroxide, lithium hydroxide, calcium hydroxide, magnesium hydroxide, aluminum hydroxide, disodium hydrogen phosphate, dipotassium hydrogen phosphate, sodium dihydrogen phosphate, diammonium hydrogen phosphate, ammonium dihydrogen phosphate, potassium dihydrogen phosphate, sodium silicate, potassium silicate, sodium carbonate, potassium carbonate, sodium bicarbonate, potassium bicarbonate, sodium borate, potassium borate, ammonia, etc.

Among them, preferable examples of the inorganic alkaline compound are sodium hydroxide and/or potassium hydroxide.

Examples of the organic alkaline compound include tetramethylammonium hydroxide, 2-hydroxyethyltrimethylammonium hydroxide, monomethylamine, dimethylamine, trimethylamine, monoethylamine, diethylamine, triethylamine, monoisopropylamine, diisopropylamine, ethanolamine, etc.

These inorganic alkaline compounds and organic alkaline compounds may be used singly or in combination of two or more compounds.

The inorganic alkaline compound or the organic alkaline compound may be liquid or solid at normal temperature. From the viewpoint of improving the operability etc., when the alkaline compound is a solid, the compound is preferably used as an aqueous solution.

The concentration of the aqueous solution of the alkaline compound is preferably 1% by mass or more and 50% by mass or less, more preferably 10% by mass or more and 40% by mass or less, from the viewpoint of improving operability and economic efficiency. By setting the concentration of the aqueous solution of the alkaline compound in such a range, the benzoic acids serving as a reaction raw material can be reacted with the halogenating agent without deteriorating the volumetric efficiency.

In the method for producing according to the present invention, it is considered that although the reason is unknown, the reactivity of the benzoic acids is improved by forming salts of benzoic acids represented by Formula (1) by using the alkaline compound.

An amount of the alkaline compound to be used may be set to an amount allowing the reaction to sufficiently proceed depending on the halogenating agent to be used and is not particularly limited. In general, the amount is preferably 0.2 equivalents or more, more preferably 0.8 to 2.5 equivalents, relative to one equivalent of the benzoic acids represented by Formula (1).

In the case of using the halogenating agent (such as the halogen molecules) generating a hydrogen halide etc. as a by-product, it may be necessary to suppress protonation of the salts of the benzoic acids by an acidic source such as a by-product hydrogen halide. Therefore, in the case of using the halogenating agent generating a hydrogen halide etc. as a by-product, preferably, 0.5 equivalents or more of alkaline compound are further used for each equivalent of the halogenating agent to be used in addition to the predetermined amount of the alkaline compound added for each equivalent of the benzoic acids represented by Formula (1).

The 2-halogenated benzoic acids acquired according to the present invention are not particularly limited and are preferably 2-bromo-4,5-dialkylbenzoic acid, 2-bromo-4,5-dialkoxybenzoic acid, 2-bromo-3,5-dialkoxybenzoic acid, 2-bromo-4-alkoxybenzoic acid, 2-bromo-5-alkoxybenzoic acid, more preferably 2-bromo-4,5-dimethylbenzoic acid, 2-bromo-4,5-diethylbenzoic acid, 2-bromo-4,5-dimethoxybenzoic acid, 2-bromo-4,5-diethoxybenzoic acid, 2-bromo-5-methoxybenzoic acid, 2-bromo-5-ethoxybenzoic acid, 2-bromo-4-methoxybenzoic acid, 2-bromo-4-ethoxybenzoic acid, 2-bromo-3,5-dimethoxybenzoic acid, and 2-bromo-3,5-diethoxybenzoic acid.

In the method for producing 2-halogenated benzoic acids of the present invention, if the benzoic acids represented by Formula (1) serving as a reaction raw material are liquid at a reaction temperature, the reaction raw material also acts as a solvent, and therefore, the reaction proceeds even without using a solvent. If the benzoic acids represented by Formula (1) are solid at a reaction temperature, the reaction may be performed by using a solvent. Examples of the solvent to be used include water, an organic solvent, and a mixed solvent of water and an organic solvent. In the present invention, from the viewpoint of economy, safety, etc., the reaction is preferably performed in water and the mixed solvent of water and an organic solvent, and is more preferably performed by using water as a solvent from an environmental perspective.

When an organic solvent is used as the reaction solvent, although a kind of the organic solvent to be used is not particularly limited, a solvent inert to the halogenating agent is preferable. Examples of such a solvent include halogenated hydrocarbons, ethers, carboxylic acids, and esters. These solvents may be used singly or in combination of two or more solvents. Examples of halogenated hydrocarbons include chlorobenzene, methylene chloride, chloroform, etc. Examples of ethers include saturated alkyl ethers and cyclic ethers, and specific examples of saturated alkyl ethers include ethyl ether, n-propyl ether, isopropyl ether, n-butyl ether, etc. Specific examples of cyclic ether include dioxane, tetrahydrofuran, etc. Examples of carboxylic acids include acetic acid, propionic acid, etc. Examples of esters include saturated alkyl ester, and specific examples of saturated alkyl ester include methyl acetate, ethyl acetate, propyl acetate, butyl acetate, methyl propionate, etc.

These solvents may be used singly, or two or more of the solvents may be mixed and used as a mixed solvent.

In the case of using the solvent, an amount of the solvent to be used is not particularly limited and, in both cases of using the solvent singly and as a mixed solvent, the amount is preferably 150 g or more, more preferably 300 g or more, per mol of the benzoic acids represented by Formula (1). The amount of the solvent to be used is preferably 10,000 g or less, more preferably 3,000 g or less, per mol of the benzoic acids represented by Formula (1). When the amount of the solvent to be used is 150 g or more per mol of the benzoic acids represented by Formula (1), stirring is facilitated and, when the amount of the solvent to be used is 10,000 g or less, a drainage treatment is facilitated, which is preferable from the viewpoint of economic efficiency and environmental protection. If the benzoic acids serving as a reaction raw material are liquid at the reaction temperature, the solvent may not be used; however, the solvent is preferably used for facilitating stirring of a reaction system.

The method for producing 2-halogenated benzoic acids of the present invention is performed with the benzoic acids represented by Formula (1) and the halogenating agent in the presence of the alkaline compound. When the reaction is performed, the reaction system is preferably stirred although the stirring may not be strong.

In the method for producing 2-halogenated benzoic acids of the present invention, the order of addition of the benzoic acids represented by Formula (1), the halogenating agent, and the alkaline compound is not particularly limited.

Furthermore, the whole amount of the benzoic acids represented by Formula (1) may be added at one step, or may be divided and added in a plurality of steps. The same applies to the halogenating agent and the alkaline compound.

For example, when the whole amount of the benzoic acids represented by Formula (1) is introduced into a reaction vessel at one step, a portion or the whole amount of the alkaline compound may be added to the reaction vessel before, during, or after the introduction of the whole amount of the benzoic acids represented by Formula (1) into the reaction vessel.

A portion or the whole amount of the halogenating agent may be added before, during, or after the introduction of a portion or the whole amount of the alkaline compound into the reaction vessel.

Although not particularly limited, the reaction temperature of the reaction between the benzoic acids and the halogenating agent in the presence of the alkaline compound is preferably −30 to 100° C., more preferably −15 to 60° C. By performing the reaction at −30° C. or higher, a sufficient reaction speed can be acquired. By performing the reaction at a temperature of 100° C. or less, the benzoic acids or the product, i.e., 2-halogenated benzoic acids, can be restrained from decomposing.

Although not particularly limited, the reaction time is typically 10 minutes to 4 hours at least after introduction of the whole amounts of the benzoic acids represented by Formula (1), the halogenating agent, and the alkaline compound into the reaction vessel.

After completion of the reaction, for example, the excessive halogenating agent may be reduced by using sodium sulfite, sodium thiosulfate, etc., before adding toluene, chlorobenzene, etc.

The reaction liquid obtained in this way is separated into an organic phase and an aqueous phase by a liquid separation operation to remove the organic phase, and the acquired aqueous phase can be isolated by crystallization (acid precipitation) or a method such as column chromatography so as to acquire 2-halogenated benzoic acids.

As described above, according to the present invention, since 2-halogenated benzoic acids can be acquired by an industrially advantageous method and the formation of regioisomers of 2-halogenated benzoic acids is suppressed in the reaction stage, 2-halogenated benzoic acids can highly selectively be produced.

EXAMPLES

The present invention will hereinafter more specifically be described with examples; however, the present invention is not limited to these examples. All the operations were performed under a nitrogen atmosphere.

Example 1

After putting 182.2 g (1.0 mol) of 3,4-dimethoxybenzoic acid into a 2,000 mL four-necked flask equipped with a stirrer, a thermometer, and a reflux cooling tube, 800 g of water was added thereto and stirred so as to disperse 3,4-dimethoxy benzoate acid. Subsequently, 273.3 g (2.05 mol) of a 30% sodium hydroxide aqueous solution was added. The liquid temperature was then reduced to 0° C., and 167.8 g (1.05 mol) of bromine was added dropwise at a liquid temperature of 0 to 5° C. Completion of the dropwise addition was followed by stirring for one hour at a liquid temperature of 0 to 5° C. After completion of the reaction, 1.28 g (0.01 mol) of sodium sulfite was added followed by addition of 100 g of toluene and raising the liquid temperature to 70° C. The organic phase was removed by a liquid separation operation, and 104.2 g (1.0 mol) of 35% hydrochloric acid was added dropwise to the acquired aqueous phase and stirred for one hour. Precipitated crystals were collected by filtration and dried under reduced pressure to acquire 238.6 g (99.9% purity, 91.3% yield) of 2-bromo-4,5-dimethoxybenzoic acid.

Example 2

After putting 210.4 g (1.0 mol) of 3,4-diethoxybenzoic acid into a 2.000 mL four-necked flask equipped with a stirrer, a thermometer, and a reflux cooling tube, 800 g of water was added thereto and stirred so as to disperse 3,4-diethoxy benzoate acid. Subsequently, 273.3 g (2.05 mol) of a 30% sodium hydroxide aqueous solution was added. The liquid temperature was then reduced to 0° C., and 167.8 g (1.05 mol) of bromine was added dropwise at a liquid temperature of 0 to 5° C. Completion of the dropwise addition was followed by stirring for one hour at a liquid temperature of 0 to 5° C. After completion of the reaction, 1.28 g (0.01 mol) of sodium sulfite was added followed by addition of 100 g of toluene and raising the liquid temperature to 70° C. The organic phase was removed by a liquid separation operation, and 104.2 g (1.0 mol) of 35% hydrochloric acid was added dropwise to the acquired aqueous phase and stirred for one hour. Precipitated crystals were collected by filtration and dried under reduced pressure to acquire 239.1 g (99.9% purity, 91.5% yield) of 2-bromo-4,5-diethoxybenzoic acid.

Example 3

After putting 152.0 g (1.0 mol) of 3-methoxybenzoic acid was into a 2.000 mL four-necked flask equipped with a stirrer, a thermometer, and a reflux cooling tube, 800 g of water was added thereto and stirred so as to disperse 3-methoxybenzoic acid. Subsequently, 273.3 g (2.05 mol) of a 30% sodium hydroxide aqueous solution was added. The liquid temperature was then reduced to 0° C., and 167.8 g (1.05 mol) of bromine was added dropwise at a liquid temperature of 0 to 5° C. Completion of the dropwise addition was followed by stirring for one hour at a liquid temperature of 0 to 5° C. After completion of the reaction, 1.28 g (0.01 mol) of sodium sulfite was added followed by addition of 100 g of toluene and raising the liquid temperature to 70° C. The organic phase was removed by a liquid separation operation, and 104.2 g (1.0 mol) of 35% hydrochloric acid was added dropwise to the acquired aqueous phase and stirred for one hour. Precipitated crystals were collected by filtration and dried under reduced pressure to acquire 237.3 g (99.9% purity, 90.8% yield) of 2-bromo-5-methoxybenzoic acid.

Example 4

After putting 152.3 g (1.0 mol) of 4-methoxybenzoic acid was into a 2,000 mL four-necked flask equipped with a stirrer, a thermometer, and a reflux cooling tube, 800 g of water was added thereto and stirred so as to disperse 4-methoxybenzoic acid. Subsequently, 273.3 g (2.05 mol) of a 30% sodium hydroxide aqueous solution was added. The liquid temperature was then reduced to 0° C., and 167.8 g (1.05 mol) of bromine was added dropwise at a liquid temperature of 0 to 5° C. Completion of the dropwise addition was followed by stirring for one hour at a liquid temperature of 0 to 5° C. After completion of the reaction, 1.28 g (0.01 mol) of sodium sulfite was added followed by addition of 100 g of toluene and raising the liquid temperature to 70° C. The organic phase was removed by a liquid separation operation, and 104.2 g (1.0 mol) of 35% hydrochloric acid was added dropwise to the acquired aqueous phase and stirred for one hour. Precipitated crystals were collected by filtration and dried under reduced pressure to acquire 238.9 g (99.9% purity, 91.4% yield) of 2-bromo-4-methoxybenzoic acid.

Example 5

After putting 182.2 g (1.0 mol) of 3,5-dimethoxybenzoic acid into a 2,000 mL four-necked flask equipped with a stirrer, a thermometer, and a reflux cooling tube, 800 g of water was added thereto and stirred so as to disperse 3,5-dimethoxybenzoic acid. Subsequently, 273.3 g (2.05 mol) of a 30% sodium hydroxide aqueous solution was added. The liquid temperature was then reduced to 0° C., and 167.80 g (1.05 mol) of bromine was added dropwise at a liquid temperature of 0 to 5° C. Completion of the dropwise addition was followed by stirring for one hour at a liquid temperature of 0 to 5° C. After completion of the reaction, 1.28 g (0.01 mol) of sodium sulfite was added followed by addition of 100 g of toluene and raising the liquid temperature to 70° C. The organic phase was removed by a liquid separation operation, and 104.2 g (1.0 mol) of 35% hydrochloric acid was added dropwise to the acquired aqueous phase and stirred for one hour. Precipitated crystals were collected by filtration and dried under reduced pressure to acquire 237.6 g (99.9% purity, 90.9% yield) of 2-bromo-3,5-dimethoxybenzoic acid.

Example 6

After putting 150.2 g (1.0 mol) of 3,4-dimethylbenzoic acid into a 2,000 mL four-necked flask equipped with a stirrer, a thermometer, and a reflux cooling tube, 800 g of water was added thereto and stirred so as to disperse 3,4-dimethylbenzoic acid. Subsequently, 273.3 g (2.05 mol) of a 30% sodium hydroxide aqueous solution was added. The liquid temperature was then reduced to 0° C., and 167.8 g (1.05 mol) of bromine was added dropwise at a liquid temperature of 0 to 5° C. Completion of the dropwise addition was followed by stirring for one hour at a liquid temperature of 0 to 5° C. After completion of the reaction, 1.28 g (0.01 mol) of sodium sulfite was added followed by addition of 100 g of toluene and raising the liquid temperature to 70° C. The organic phase was removed by a liquid separation operation, and 104.2 g (1.0 mol) of 35% hydrochloric acid was added dropwise to the acquired aqueous phase and stirred for one hour. Precipitated crystals were collected by filtration and dried under reduced pressure to acquire 230.8 g (99.9% purity, 88.3% yield) of 2-bromo-4,5-dimethoxybenzoic acid.

Example 7

After putting 533.3 g (4.00 mol) of a 30% sodium hydroxide aqueous solution into a 1,000 mL four-necked flask equipped with a stirrer, a thermometer, and a reflux cooling tube, 319.6 g (2.00 mol) of bromine was added dropwise in a range of liquid temperature of −5 to 5° C. to acquire 852.9 g of a sodium hypobromite aqueous solution.

After putting 182.2 g (1.0 mol) of 3,4-dimethoxybenzoic acid into a 2,000 mL four-necked flask equipped with a stirrer, a thermometer, and a reflux cooling tube, 800 g of water was added thereto and stirred so as to disperse 3,4-dimethoxybenzoic acid. To this dispersion, 554.4 g (corresponding to 1.30 mol of bromine) of the sodium hypobromite aqueous solution acquired at the previous step was added dropwise at a liquid temperature of 0 to 5° C. After stirring for one hour at a liquid temperature of 0 to 5° C., 8.82 g (0.07 mol) of sodium sulfite was added followed by addition of 100 g of toluene and raising the liquid temperature to 70° C. The organic phase was removed by a liquid separation operation, and 104.2 g (1.0 mol) of 35% hydrochloric acid was added dropwise to the acquired aqueous phase and stirred for one hour. Precipitated crystals were collected by filtration and dried under reduced pressure to acquire 233.4 g (99.9% purity, 89.3% yield) of 2-bromo-4,5-dimethoxybenzoic acid.

Example 8

After putting 182.2 g (1.0 mol) of 3,4-dimethoxybenzoic acid into a 2,000 mL four-necked flask equipped with a stirrer, a thermometer, and a reflux cooling tube, 800 g of water was added thereto and stirred so as to disperse 3,4-dimethoxybenzoic acid. Subsequently, 133.3 g (1.00 mol) of a 30% sodium hydroxide aqueous solution was added. The liquid temperature was then reduced to 0° C. and 186.9 g (1.05 mol) of N-bromosuccinimide (NBS) was added at a liquid temperature of 0 to 5° C. Completion of the dropwise addition was followed by stirring for one hour at a liquid temperature of 0 to 5° C. After completion of the reaction, 1.28 g (0.01 mol) of sodium sulfite was added followed by addition of 100 g of toluene and raising the liquid temperature to 70° C. The organic phase was removed by a liquid separation operation, and 104.2 g (1.0 mol) of 35% hydrochloric acid was added dropwise to the acquired aqueous phase and stirred for one hour. Precipitated crystals were collected by filtration and dried under reduced pressure to acquire 238.1 g (99.9% purity, 91.1% yield) of 2-bromo-4,5-dimethoxybenzoic acid.

Example 9

After putting 182.2 g (1.0 mol) of 3,4-dimethoxybenzoic acid into a 2,000 mL four-necked flask equipped with a stirrer, a thermometer, and a reflux cooling tube, 800 g of water was added thereto and stirred so as to disperse 3,4-dimethoxybenzoic acid. Subsequently, 133.3 g (1.00 mol) of a 30% sodium hydroxide aqueous solution was added. The liquid temperature was then reduced to 0° C., and 150.1 g (0.53 mol (1.05 equivalent)) of 1,3-dibromo-5,5-dimethylhydantoin (DBH) was added at a liquid temperature of 0 to 5° C. Completion of the dropwise addition was followed by stirring for one hour at a liquid temperature of 0 to 5° C. After completion of the reaction, 1.28 g (0.01 mol) of sodium sulfite was added followed by addition of 100 g of toluene and raising the liquid temperature to 70° C. The organic phase was removed by a liquid separation operation, and 104.2 g (1.0 mol) of 35% hydrochloric acid was added dropwise to the acquired aqueous phase and stirred for one hour. Precipitated crystals were collected by filtration and dried under reduced pressure to acquire 239.4 g (99.9% purity, 91.6% yield) of 2-bromo-4,5-dimethoxybenzoic acid.

Example 10

After putting 182.2 g (1.0 mol) of 3,4-dimethoxybenzoic acid into a 2,000 mL four-necked flask equipped with a stirrer, a thermometer, and a reflux cooling tube, 800 g of water was added thereto and stirred so as to disperse 3,4-dimethoxybenzoic acid. Subsequently, 133.3 g (1.00 mol) of a 30% sodium hydroxide aqueous solution was added. The liquid temperature was then reduced to 0° C., and 167.8 g (1.05 mol) of bromine was added dropwise at a liquid temperature of 0 to 5° C. Completion of the dropwise addition was followed by stirring for one hour at a liquid temperature of 0 to 5° C. After completion of the reaction, 1.28 g (0.01 mol) of sodium sulfite was added followed by addition of 100 g of toluene and raising the liquid temperature to 70° C. The organic phase was removed by a liquid separation operation, and 104.2 g (1.0 mol) of 35% hydrochloric acid was added dropwise to the acquired aqueous phase and stirred for one hour. Precipitated crystals were collected by filtration and dried under reduced pressure to acquire 177.2 g (99.9% purity, 67.8% yield) of 2-bromo-4,5-dimethoxybenzoic acid.

Comparative Example 1

After putting 182.2 g (1.0 mol) of 3,4-dimethoxybenzoic acid into a 2,000 mL four-necked flask equipped with a stirrer, a thermometer, and a reflux cooling tube, 800 g of water was added thereto and stirred so as to disperse 3,4-dimethoxybenzoic acid. The liquid temperature was reduced to 0° C., and 167.8 g (1.05 mol) of bromine was added dropwise at a liquid temperature of 0 to 5° C. Completion of the dropwise addition was followed by stirring for one hour at a liquid temperature of 0 to 5° C. When the reaction solution was analyzed by liquid chromatography, 77% (0.77 mol) of 3,4-dimethoxybenzoic acid had remained. The liquid temperature was raised to 60° C. and the solution was stirred for six hours. Subsequently, 1.28 g (0.01 mol) of sodium sulfite was added followed by addition of 100 g of toluene and raising the liquid temperature to 70° C. The organic phase was removed by a liquid separation operation, and 104.2 g (1.0 mol) of 35% hydrochloric acid was added dropwise to the acquired aqueous phase and stirred for one hour. Precipitated crystals were collected by filtration and dried under reduced pressure to obtain 29.0 g (79.3% purity, 8.8% yield) of 2-bromo-4,5-dimethoxybenzoic acid.

Comparative Example 2

According to the method described in Patent Document 2, 3650 mL of 35% hydrochloric acid was put into a 10,000 mL four-necked flask equipped with a stirrer, a thermometer, and a reflux cooling tube, and 182.2 g (0.14 mol) of 3,4-dimethoxybenzoic acid was added and stirred so as to disperse 3,4-dimethoxybenzoic acid. Subsequently, at the liquid temperature of 25° C., 167.8 g (1.05 mol) of bromine was added dropwise at a liquid temperature of 20 to 30° C. Completion of the dropwise addition was followed by stirring for seven hours at a liquid temperature of 20 to 30° C. Subsequently, 3650 mL of water was added and stirred for one hour before precipitated crystals were collected by filtration. Drying under reduced pressure results in 261.1 g (90.3% purity, 90.3% yield) of 2-bromo-4,5-dimethoxybenzoic acid.

The conditions and reaction results of Examples 1 to 10, and Comparative Examples 1, 2 are shown in Table 1. In Table 1, Compounds A to D are typical regioisomers (having different halogenation positions). Specifically, A denotes a 1,2-dibromo compound generated by a decarboxylation reaction; B denotes a 3-bromo-substituted compound; C denotes a 2,3-dibromo-substituted compound; and D denotes a 2,6-dibromo-substituted compound. For A to D described above, the acquired aqueous phase was analyzed by liquid chromatography to calculate a production amount thereof in each of Examples and Comparative Examples ("N.D." in the table means Not Detectable).

For example, as can be understood from the Hunsdiecker reaction, it is known that a decarboxylation reaction progresses when carboxylic acids such as benzoic acids used in the present invention are reacted with bromine in general. The progress of the decarboxylation reaction may increase the necessary halogenating agent such as bromine or reduce the yield of the intended compound.

However, according to the results of Examples 1 to 10 of the present invention, since the yield of the acquired 2-halogenated benzoic acids is high and the problem of the reduced yield of the intended compound is not generated, it can be understood that the decarboxylation reaction is suppressed or has made almost no progress.

Therefore, as is apparent from Examples 1 to 10 of the present invention, the method of producing according to the present invention can suppress the decarboxylation reaction, has high regioselectivity, and can produce 2-halogenated benzoic acids in high yield.

Furthermore, by comparing the results of Examples of the present invention with the result of Comparative Example 1, it is found that by using the alkaline compound in a bromination reaction of benzoic acids, 2-halogenated benzoic acids can be acquired in short time and in high yield.

According to the results of Examples of the present invention and Comparative Example 2, 2-halogenated benzoic acids are acquired in high yield. However, in Examples of the present invention, the halogenation reaction extremely promptly proceeds, and the acids can be acquired highly selectively and in the same level of yield.

Additionally, according to Comparative Example 2, a plurality of regioisomers (B, C, D, etc. in the table) halogenated at positions other than the 2-position of the benzene ring are generated as by-product. These regioisomers have physical properties similar to the intended compound (2-halogenated benzoic acid) and are therefore difficult to separate respectively from the intended compound. However, the compounds generated as by-products in Examples 1 to 10 are a decarbonized product with the carboxylic acid moiety eliminated from 2-halogenated benzoic acids and a dibromo compound with bromine further added to the decarbonized product (A in the table) and can easily be removed by a liquid separation operation etc. because of physical properties different from the intended compound.

Furthermore, according to Comparative Example 2, 3650 mL of 35% hydrochloric acid and 3650 mL of water (7300 mL in total) are used per mol of benzoic acids. However, for example, Examples 8 to 10 require only 103 mL of a 30% sodium hydroxide aqueous solution and 800 mL of water (903 mL in total) and are obviously industrially advantageous also from the viewpoint of volumetric efficiency.

TABLE 1

|  | Starting material | Halogenating agent Type | Amount used [mol] | Alkaline compound Type | Amount used [mol] | Reaction time [hr] | Production yield of compounds [%] vs. Starting material Intended compound | A | B | C | D |
|---|---|---|---|---|---|---|---|---|---|---|---|
| Example 1 | 3,4-dimethoxybenzoic acid | Br2 | 1.05 | NaOH | 2.05 | 1 | 91.3 | 6.9 | N.D. | N.D. | N.D. |
| Example 2 | 3,4-diethoxybenzoic acid | Br2 | 1.05 | NaOH | 2.05 | 1 | 91.5 | 6.7 | N.D. | N.D. | N.D. |
| Example 3 | 3-methoxybenzoic acid | Br2 | 1.05 | NaOH | 2.05 | 1 | 90.8 | 7.2 | N.D. | N.D. | N.D. |
| Example 4 | 4-methoxybenzoic acid | Br2 | 1.05 | NaOH | 2.05 | 1 | 91.4 | 6.8 | N.D. | N.D. | N.D. |
| Example 5 | 3,5-dimethoxybenzoic acid | Br2 | 1.05 | NaOH | 2.05 | 1 | 90.9 | 7.0 | N.D. | N.D. | N.D. |
| Example 6 | 3,4-dimethylbenzoic acid | Br2 | 1.05 | NaOH | 2.05 | 1 | 88.3 | 9.8 | N.D. | N.D. | N.D. |
| Example 7 | 3,4-dimethoxybenzoic acid | NaBrO | 1.30 | —* | | 1 | 89.3 | 9.8 | N.D. | N.D. | N.D. |
| Example 8 | 3,4-dimethoxybenzoic acid | NBS | 1.05 | NaOH | 1.00 | 1 | 91.1 | 6.7 | N.D. | N.D. | N.D. |
| Example 9 | 3,4-dimethoxybenzoic acid | DBH | 0.53 | NaOH | 1.00 | 1 | 91.6 | 7.0 | N.D. | N.D. | N.D. |
| Example 10 | 3,4-dimethoxybenzoic acid | Br2 | 1.05 | NaOH | 1.00 | 1 | 67.8 | 18.6 | N.D. | N.D. | N.D. |
| Comparative Example 1 | 3,4-dimethoxybenzoic acid | Br2 | 1.05 | — | — | 6 | 8.8 | 12.4 | 0.6 | 0.9 | 0.4 |
| Comparative Example 2 | 3,4-dimethoxybenzoic acid | Br2 | 1.05 | Concentrated hydrochloric acid | | 7 | 90.3 | 3.2 | 1.8 | 2.0 | 1.3 |

*NaBrO acts as an alkaline compound.

The invention claimed is:

1. A method for producing 2-halogenated benzoic acids comprising: reacting benzoic acids represented by Formula (1)

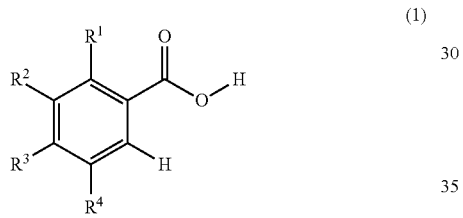

in Formula (1), $R^1$ and $R^4$ each independently represent a hydrogen atom, and $R^2$ represents a hydrogen atom, an alkyl group having the carbon number of 1 to 18, or an alkoxy group having the carbon number of 1 to 18, and $R^3$ represents an alkoxy group having the carbon number of 1 to 18 with a halogenating agent in the presence of an alkaline compound at a reaction temperature of 0 to 5° C.

* * * * *